(12) United States Patent
Dias et al.

(10) Patent No.: US 8,109,913 B2
(45) Date of Patent: Feb. 7, 2012

(54) COILED WIRE FOR THE CONTROLLED RELEASE OF DRUGS TO THE EYE

(75) Inventors: Aylvin Jorge Angelo Athanasius Dias, Maastricht (NL); Levinus Hendrik Koole, Gulpen (NL); Rachel Theodora Pijls, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/994,934

(22) PCT Filed: Jun. 30, 2006

(86) PCT No.: PCT/EP2006/006355
§ 371 (c)(1),
(2), (4) Date: Jul. 19, 2008

(87) PCT Pub. No.: WO2007/006427
PCT Pub. Date: Jan. 18, 2007

(65) Prior Publication Data
US 2009/0143747 A1    Jun. 4, 2009

(30) Foreign Application Priority Data

Jul. 11, 2005  (EP) .................................... 05076580
Sep. 27, 2005  (EP) .................................... 05077210

(51) Int. Cl.
*A61M 35/00* (2006.01)
*A61F 2/00* (2006.01)
*A61F 9/00* (2006.01)

(52) U.S. Cl. ......................... 604/289; 424/427; 606/107

(58) Field of Classification Search .... 604/890.1–892.1, 604/289; 424/423, 426, 427
See application file for complete search history.

(56) References Cited

U.S. PATENT DOCUMENTS

| | | | |
|---|---|---|---|
| 5,690,667 A * | 11/1997 | Gia | 606/191 |
| 6,478,776 B1 * | 11/2002 | Rosenman et al. | 604/164.01 |
| 6,719,750 B2 * | 4/2004 | Varner et al. | 604/289 |
| 7,491,214 B2 * | 2/2009 | Greene et al. | 606/195 |
| 2006/0024350 A1 * | 2/2006 | Varner et al. | 424/427 |

OTHER PUBLICATIONS

International Search Report for PCT/EP2006/006355 mailed Aug. 29, 2006.
Written Opinion for PCT/EP2006/006355 mailed Aug. 29, 2006.

\* cited by examiner

*Primary Examiner* — Kevin C Sirmons
*Assistant Examiner* — Imani Hayman
(74) *Attorney, Agent, or Firm* — Nixon & Vanderhye P.C.

(57) ABSTRACT

This invention is in the area of medical devices, in particular in the area of medical devices for drug delivery, more in particular for controlled release of drugs to the eye. Delivery of drugs to the anterior side of the eye is routinely done with eye drops, but this method results in low bioavailability and low patient compliance. Devices that address these problems have been described for the delivery of drugs to the eye. One of such devices, called the OphthaCoil, consists of a thin metallic wire, which is coiled and carries a drug-loaded adherent hydrogel coating on its surface. Surprisingly it has now been found that the drug loading capacity can be dramatically increased by filling the lumen of the coil with micro-particles such as microspheres that contain the drug of choice.

16 Claims, 7 Drawing Sheets

COILED WIRE FOR THE CONTROLLED RELEASE OF DRUGS TO THE EYE

This application is the U.S. national phase of International Application No. PCT/EP2006/006355 filed 30 Jun. 2006 which designated the U.S. and claims priority to European Patent Application Nos. 05076580.9 filed 11 Jul. 2005 and 05077210.2 filed 27 Sep. 2005, the entire contents of each of which are hereby incorporated by reference.

BACKGROUND

This invention is in the area of medical devices, in particular in the area of medical devices for drug delivery, more in particular for controlled release of drugs to the eye.

Delivery of drugs to the anterior side of the eye is routinely done with eye drops, but this method results in low bioavailability and low patient compliance. Devices that address these problems have been described for the delivery of drugs to the eye. One of such devices, called the OphthaCoil, consists of a thin metallic wire, which is coiled and carries a drug-loaded adherent hydrogel coating on its surface. The drug is then released in a more or less controlled fashion in vitro as well as in vivo (Pijls et al., Eur. J. Pharm. Biopharm. 59, 283 (2005)).

By using this device, anti-microbial drug levels in the tear fluid of dogs could well be maintained above the MIC-values of relevant bacteria after 16 hours, using pradofloxacin, a very potent anti-microbial drug. The devices were well tolerated, but may be lost when left in the eye overnight.

The drug loading capacity of the OphthaCoil, however, becomes the limiting factor when less potent drugs are to be delivered to the eye. Several strategies have been suggested to solve this problem. First, it was suggested to fill the coil with a hydrogel. When polymerizing a hydrogel in the lumen itself, it appeared that the coil lost its flexibility. The loss of flexibility is detrimental for the patient, since the device is no longer tolerated when rigid. The solution was found in that a number of straight wires, made of the same material as the wires constituting the coil, was inserted into the coil. The straight wires were coated with the same coating as the coil and so increased the drug load of the assembled device. The coils thereby lost some of their flexibility by that process.

Therefore, it remains desirable to increase the drug loading capacity of such coiled devices while maintaining or improving the flexibility.

SUMMARY

Surprisingly it has now been found that the drug loading capacity can be dramatically increased by introducing micro-particles such as micro-spheres or microbeads that contain the drug of choice into the lumen of the coil. A coil or coiled wire as used herein defines a wound structure with a distal and proximal end and a lumen inside the windings of the wire. The invention therefore relates to a coiled wire with a distal and proximal end and defining a lumen inside the windings of the wire wherein said lumen contains micro-particles comprising an active component such as a drug.

Advantageously, the coiled wire according to the invention comprises a hydrophilic coating.

When pHEMA (poly-(2-hydroxyethyl)methacrylate) micro-particles loaded with fluorescein sodium salt as a model for a drug were introduced into the lumen of an OphthaCoil device, a controlled release pattern of the dye could be demonstrated. It was found that the dye was quickly released from the hydrophilic coating on the outside of the coil, whereas the dye in the micro-particles was released more slowly. In this way the release of a drug may be influenced and dosed more reliably in comparison to the prior art technology. The invention therefore also relates to a coiled wire comprising micro-particles that consist of a hydrophilic polymer, such as pHEMA and/or NVP.

Preferably, the micro-particles for use in the invention are micro-spheres and/or made of a polymer, preferably a biodegradable polymer, even more preferably a porous polymer wherein the drugs are contained inside the micro-particle.

Moreover, the invention also relates to the use of a coiled wire according to the invention for controlled drug release.

Even more surprisingly, the coils filled with micro-particles had an exceptionally good flexibility, far better than the devices filled with straight wires. They were as flexible as the unfilled coils.

It is important to control the diameter of the micro-particles. The particles should not be too small in order to prevent leakage of complete particles into the eye through the windings of the coil. They should also be small enough to be filled into the lumen when in the dry state.

DETAILED DESCRIPTION

Examples

Example 1

Preparation of the OphthaCoil Device

Figure 1:
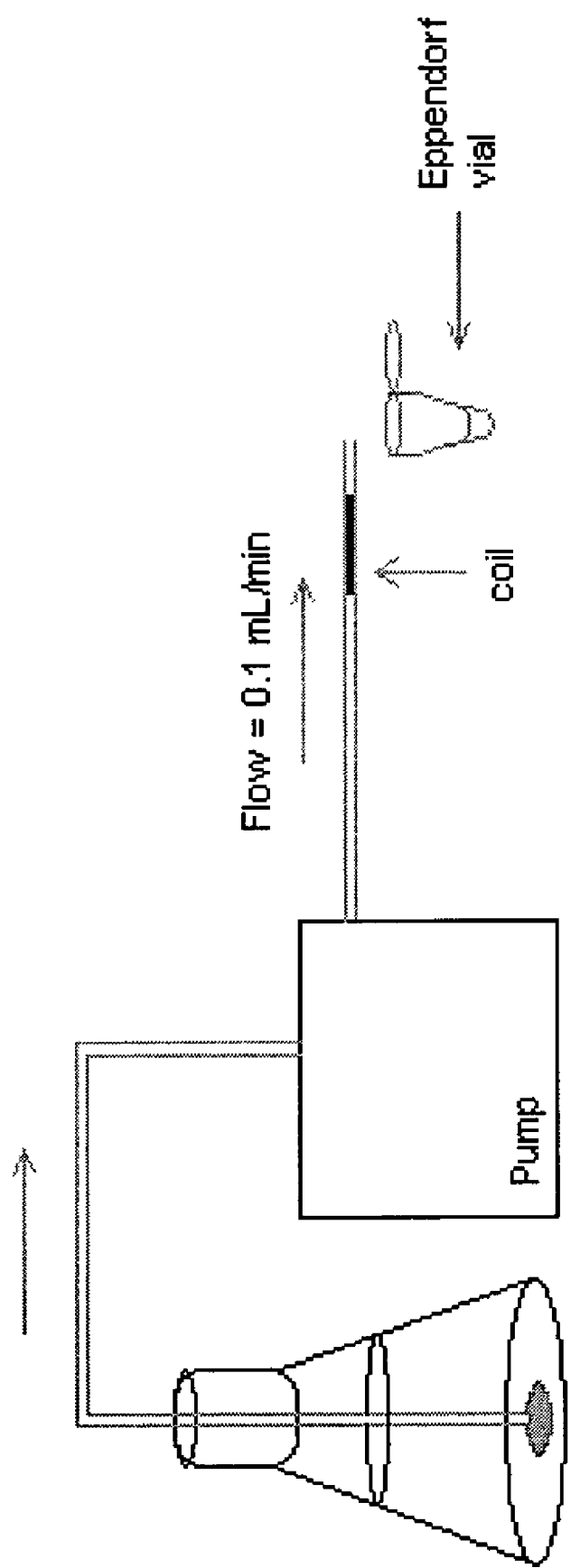
FIG. 1. Experimental set up of the drug and dye release experiments

The OphthaCoil is a device for the controlled delivery of drugs to the anterior side of the eye. The device consists of a drug-loaded adherent hydrogel (Slipskin®) on a thin metallic wire, which is coiled (Hanssen et al., J. Biomed. Mater. Res (Appl. Biomater.) 48, 820 (1999)), as described in U.S. Pat. No. 6,086,547. The metallic wire had a diameter of 76 µm and was first coated with the primer polyethersulfone (PES). Then the wire was coated with a solution of Slipskin® with a drug dissolved. This resulted in a diameter of ±85 µm for wire and coating. Finally the coated wire was coiled around a core wire of 432 µm and cut into pieces of 15 mm in length. The ends of the coil were closed with a polymeric cap and the device was gas-sterilized before use.

Several release studies have been done with the Ophtha-Coil. In vitro release studies of the dye fluorescein, and the antibiotics chloramphenicol and pradofloxacin, show that a dye or drug can be released for over 48 hours, and show that the drugs are still active when released from the coating. In vivo study with a device loaded with the pupil widening agent atropine shows that mydriasis can be obtained and in vivo studies with dogs show that the device is well tolerated in the canine eye and that pradofloxacin can be detected at a concentration well above the MIC-value in the tear fluid for at least 16 hours (Pijls et al., Biomed. Mater. Eng. 14(4), 383 (2004); Pijls et al., Eur. J. Pharm. Biopharm. 59(2), 283 (2005)).

This invention is concerned with increasing the capacity of the device by filling the lumen of the coil with drug-loaded microparticles, such as pHEMA-microspheres. pHEMA is used for its high water uptake and it is a well-known material in opthalmology (Karlgard et al., Int. J. Pharm. 257, 141 (2003); Gulsen et al., Invest. Opthalmol. Vis. Sci. 45, 2342 (2004)). The result of filling the lumen with drug-loaded microspheres is a device with two release systems: fast release of a drug from the coating of the coiled wire and slow release of the microspheres inside the lumen of the device. Most importantly, filling the lumen with microspheres does not compromise the coil's flexibility. Moreover, the device can also be loaded with different drugs.

Example 2

Preparation of the Microspheres

Chemicals were purchased from Acros Organics, Belgium, unless stated otherwise. Two types of microspheres are exemplified herein; pHEMA microspheres and pHEMA/NVP microspheres.

The pHEMA-microspheres were prepared by the suspension polymerization of the monomer HEMA in an aqueous medium containing 17% w/w sodium chloride and 0.672% w/w magnesium hydroxide. The suspension stabilizer magnesium hydroxide was prepared in situ by precipitation from magnesium chloride using sodium hydroxide. The dispersed phase contained the monomer HEMA (96.8% w/w), the cross-linker tetra-ethyleneglycol-dimethacrylate (tetra-EGDM) (3% w/w) (Fluka Chemie, the Netherlands) and the initiator 2,2'-azobis(2-methylpropionitrile) (AIBN) (0.2% w/w) (Jayakrishnan et al., J. Biomed. Mater. Res. 24, 913 (1990); Jayakrishnan et al., Polymer 31, 1339 (1990)).

The reaction, based on the description of Jayakrishnan, was carried out as follows. A 250 mL round-bottomed flask fitted with a stirrer of half-moon type was charged with a solution containing the calculated quantity of sodium chloride and magnesium chloride in 70 mL of water. The flask was heated to 70° C. in a thermostatic oil bath and the required amount of sodium hydroxide was added in 15 mL of water with stirring to precipitate the magnesium hydroxide. The temperature was raised to 80° C. and the monomer with cross-linker and initiator (total weight of 36 g) was introduced drop wise into the flask. The suspension was stirred at 150 rpm for 4 h.

After the reaction, the magnesium hydroxide was dissolved by adding dilute hydrochloric acid (Merck, Germany). The beads were washed several times with distilled water. Then they were dried under vacuum in an oven at 35° C. and sieved into different fractions using standard test sieves (Retsch, Germany).

With monomers such as HEMA that are highly water soluble, dispersion of the monomer into droplets has to be carried out in concentrated salt solutions in which the distribution coefficient of the monomer is very low. By varying the stabilizer concentration and stirring speed the size of the beads can be varied (Jayakrishnan et al., J. Biomed. Mater. Res. 24, 913 (1990)).

The pHEMA/NVP spheres were prepared via the same method, as described above. Here the dispersed phase consisted not only of the monomer HEMA, but it consisted of 70/30% w/w HEMA/NVP. The addition of NVP to the microspheres resulted in more hydrophilic microspheres. The suspension polymerization was carried out as described above. The yield of both reactions was 75% for the pHEMA spheres and 95% for the pHEMA/NVP spheres. The distribution of the different beads into sizes is given in table 1.

TABLE 1

Size distribution of the microspheres

| pHEMA | | pHEMA/NVP | |
| --- | --- | --- | --- |
| size (μm) | % w/w | size (μm) | % w/w |
| <200 | 19.6% | <200 | 0.5% |
| 200-300 | 28.4% | 200-300 | 15.2% |
| 300-425 | 36.2% | 300-425 | 34.8% |
| 425-1000 | 15.6% | 425-600 | 46.7% |
| >1000 | 0.2% | >600 | 2.7% |

Example 3

Swelling and Drug Loading of Microparticles

The lumen of the OphthaCoil as prepared in Example 1 was appr. 450 μm in diameter, so in the following experiments the fraction of beads of 300-425 μm was used. To determine the diameters of the different beads, dry or swollen, a light microscope (Nikon Eclipse 800) and a program for image processing and analysis (ImageJ, version 1.32j) were used. First the diameters of dry microspheres (n=50) were measured. Then the spheres were put in Simulated Lacrimal Fluid (SLF) (Paulsson et al., J. Pharm. Sci. 90(9) 1216 (2001)). The diameters of the swollen microspheres were measured after 4 h and finally the total volume swelling was calculated by the formula:

Vol. Swelling=$r_{wet}^3/r_{dry}^3 \times 100\%$, with $r$=radius of the sphere.

Also the swelling of the microspheres in time was investigated. To do this, a dry microsphere was put under the microscope. Several drops of SLF were put onto the microsphere and photos are taken at different time points between 0 and 45 minutes. The radius of the microsphere can then be measured in time.

The average diameters of the dry microspheres (n≧300) and the swelling times are given in Table 2. Also the volume swelling is given in the table.

TABLE 2

Average size and swelling of the different microspheres

| | pHEMA | pHEMA/NVP |
| --- | --- | --- |
| Average size diameter | 195 μm | 300 μm |
| Swelling time | 20 minutes | 10 minutes |
| Diameter swelling | 13.5% | 15% |
| Volume swelling | 50% | 52% |

In the following experiments the dye fluorescein sodium salt is used to load the microspheres. The dye serves as a model compound of a drug. The microspheres were put in a vial with a concentrated solution of fluorescein sodium salt (75 mM) for 24 hours. The excess of the solution was removed from the vial and the spheres were lyophilized. The dry spheres contained the dye, as could be inferred from their orange color. Then the coils could be filled with dye-loaded microspheres through a tiny funnel.

Example 4

Release Characteristics of Dye-Loaded Microspheres

The release of fluorescein sodium salt from the device was measured in three different experiments in fourfold for both types of microspheres. In the different experiments the drug loading of the coils was different. This is explained in table 3.

TABLE 3

Types of drug loading of the device.

| Experiment | Coil | Lumen |
|---|---|---|
| A | Drug-loaded coating | No microspheres |
| B | Not loaded coating | Drug-loaded microspheres |
| C | Drug-loaded coating | Drug-loaded microspheres |

The experimental set up is shown in FIG. 1. Simulated lacrimal fluid was pumped through a tube, with an inner diameter of 1 mm. The flow was set on 0.1 mL/min. A coil was placed on the end of the tube and fractions of appr. 150 µL were collected in Eppendorf vials at different time points. The concentration of fluorescein sodium in these fractions was measured with a spectrofluorimeter, using a 96-wells plate and a calibration curve.

Figure 2A:
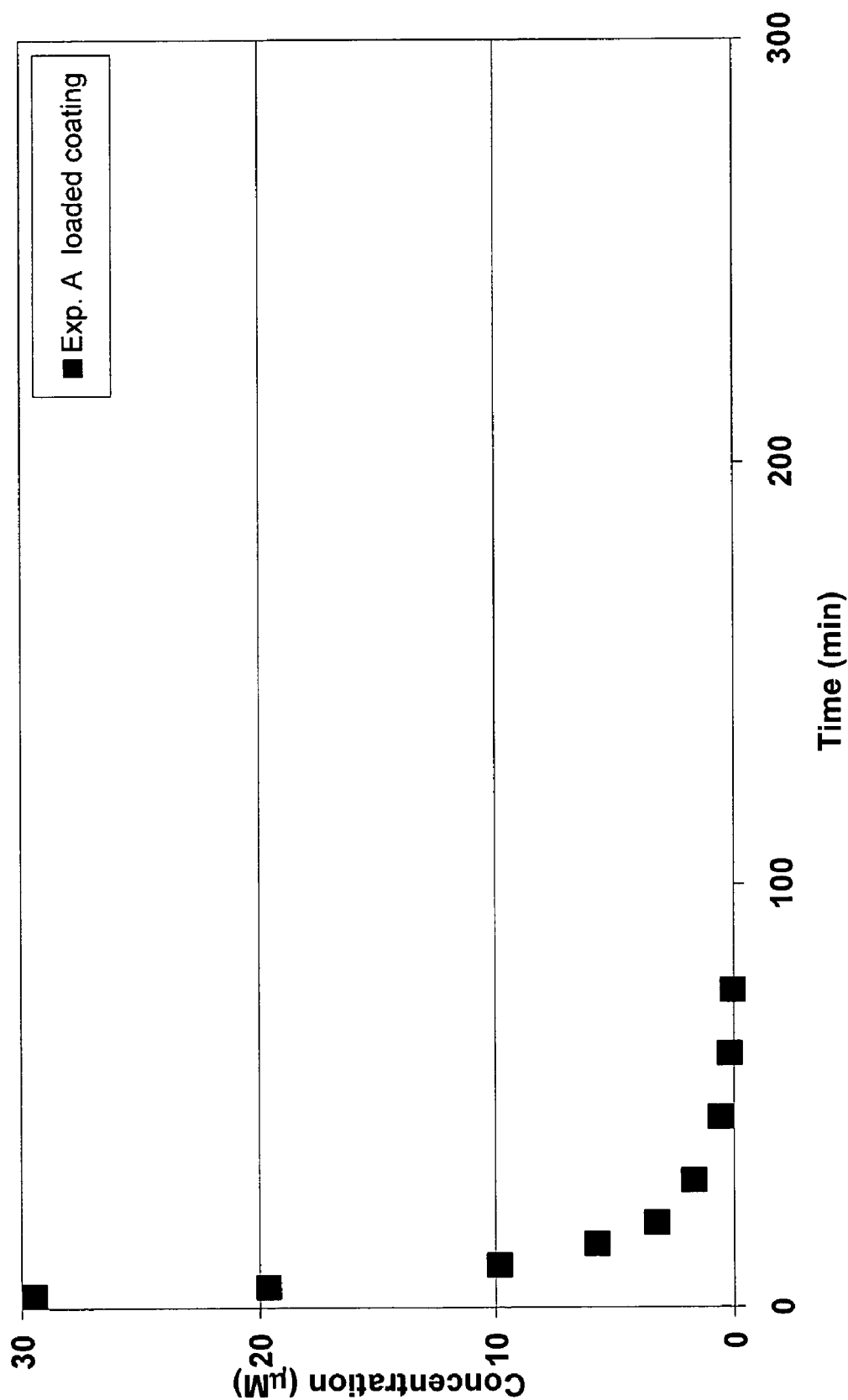
FIG. 2A. Release curve of a fluorescein loaded coil
Figure 2B:
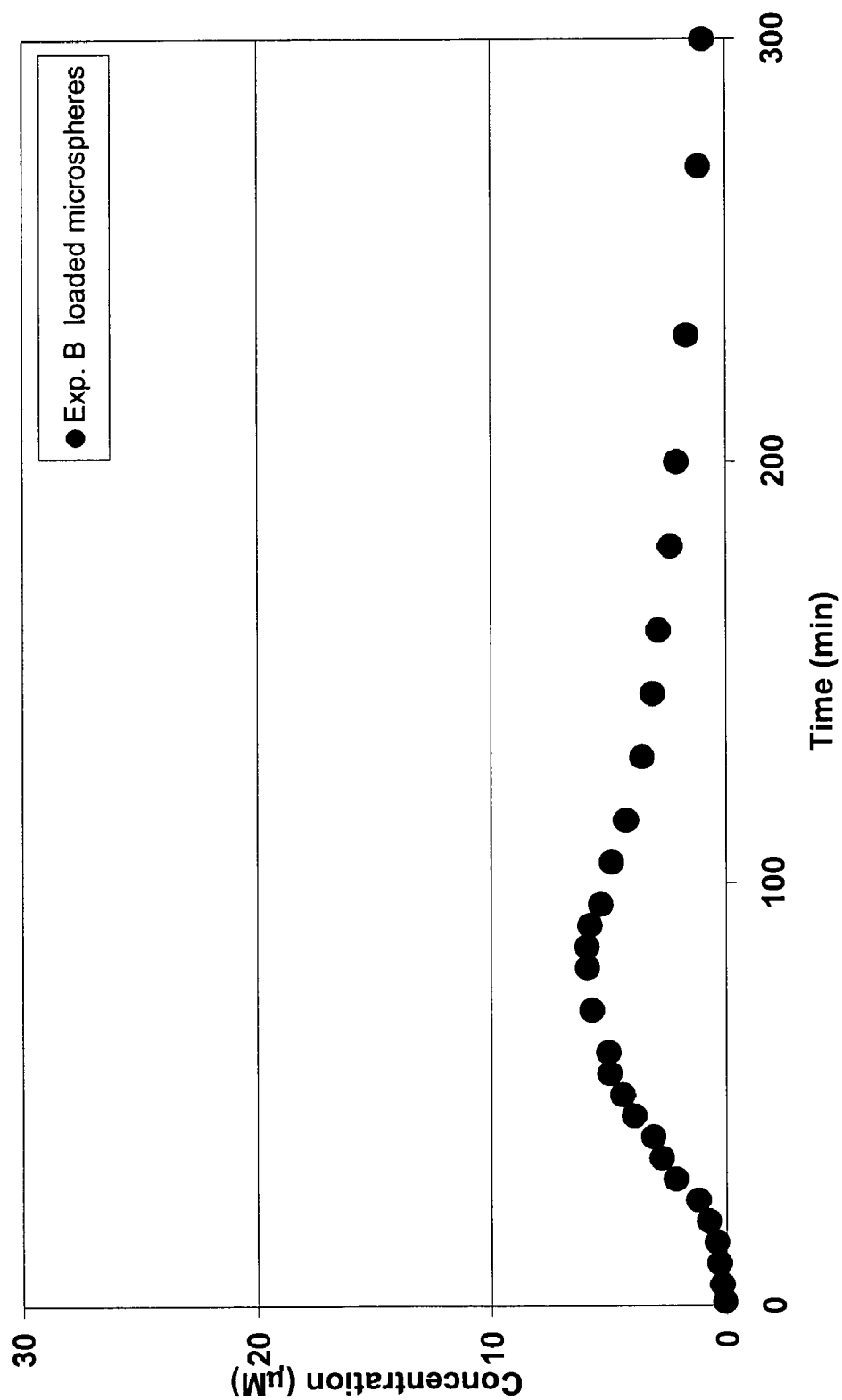
FIG. 2B. Release curve of fluorescein from loaded microspheres in an unloaded coil FIG. 2C. Release curve of fluorescein from loaded microspheres in a loaded coil FIG. 3. Release of fluorescein from two different types of microspheres in the lumen of the coil FIG. 4. The set up of the three-point bending test FIG. 5. The results of the three-point bending test, showing the average values obtained for the three different coils (n=8)
Figure 2C:
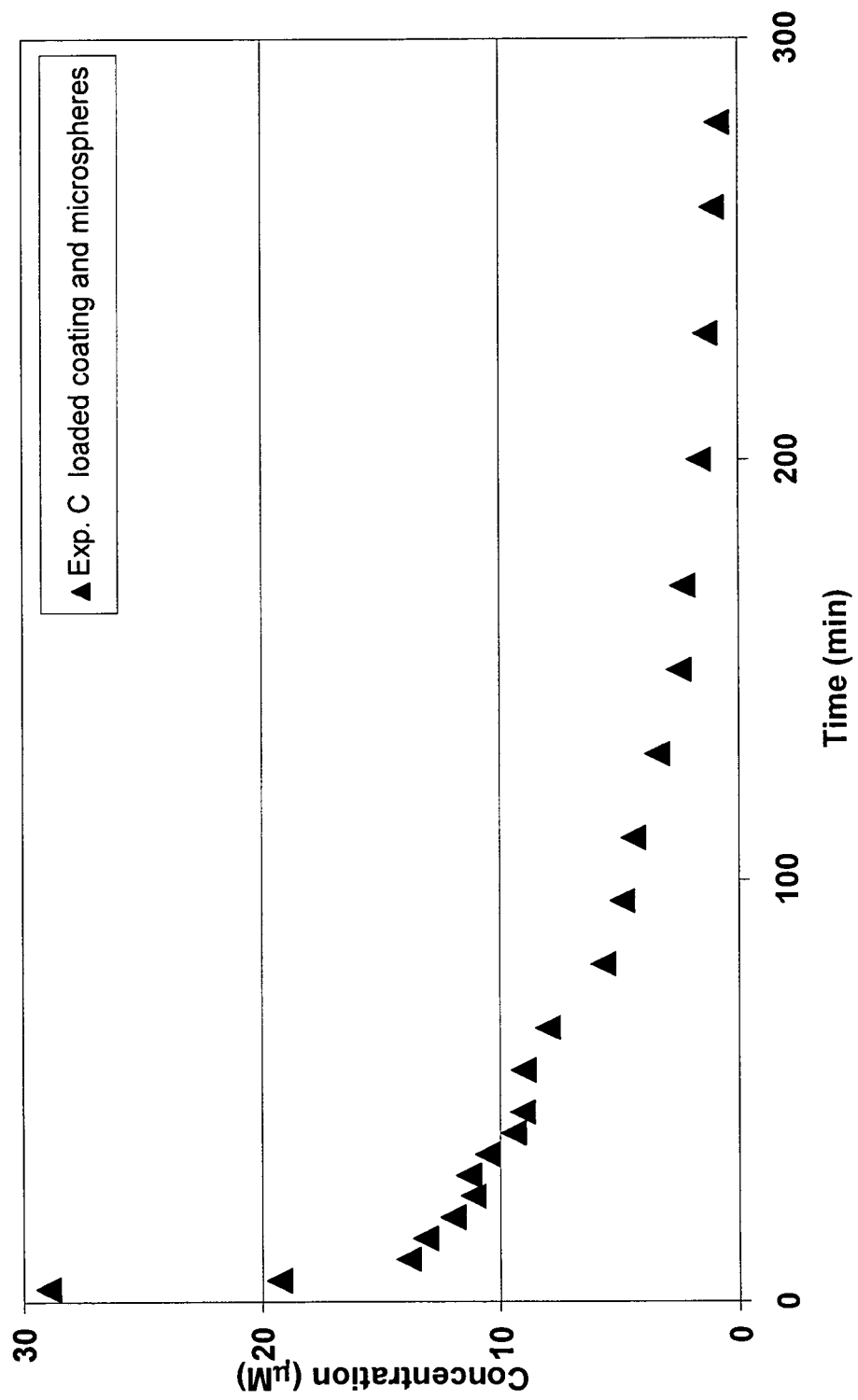

The curves of the release experiments based on pHEMA microspheres are given in FIG. 2. It may be concluded that the capacity of the OphthaCoil can be increased by filling the lumen of the coil with drug-loaded microspheres. The dye fluorescein sodium salt was released for over 5 hours from the device.

Figure 3:
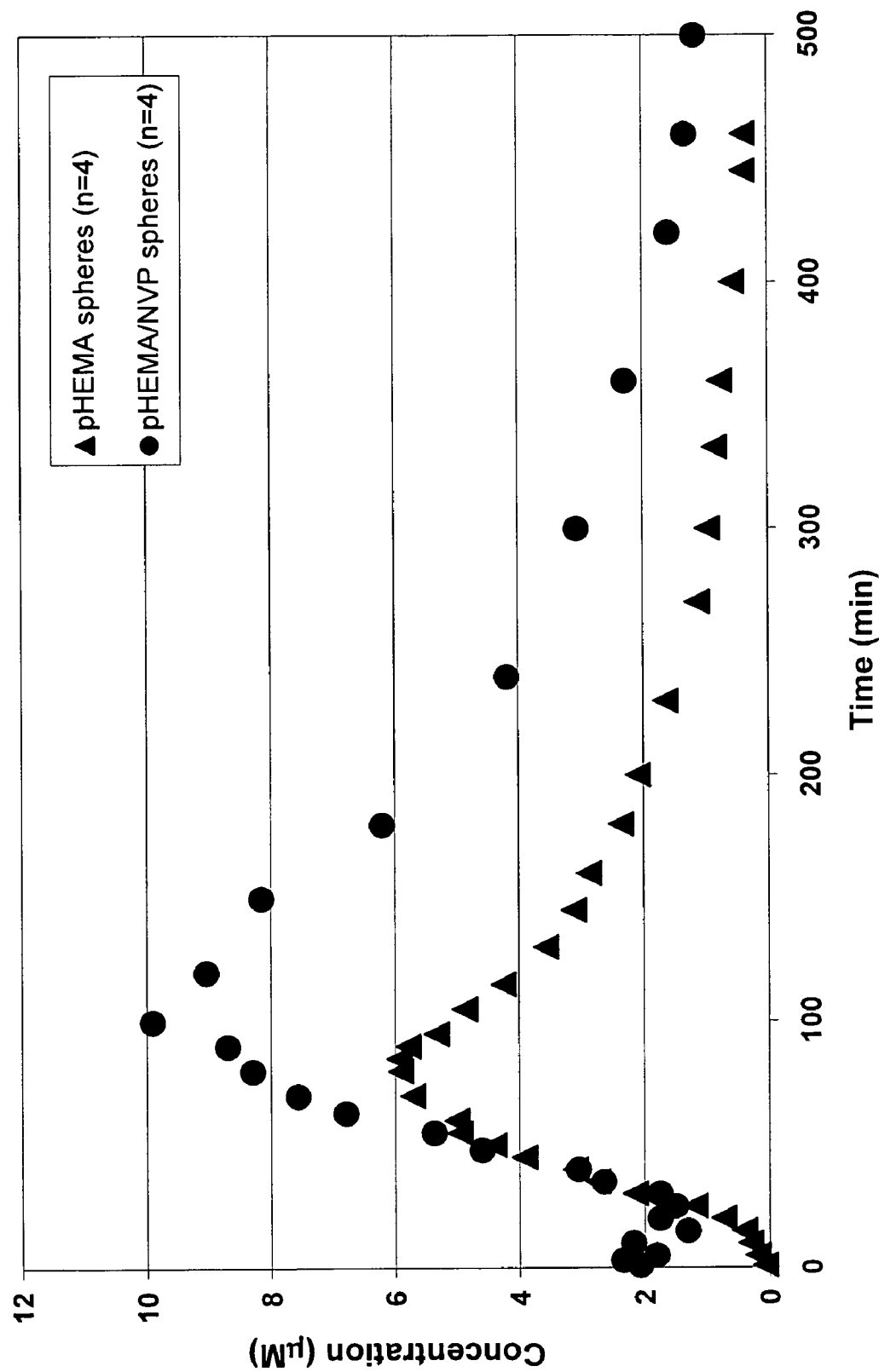

To compare both types of microspheres, the release of experiment B (no drug-loaded coating, only drug-loaded microspheres) is given in FIG. 3. The total release of fluorescein sodium was determined by calculating the area under the curve (AUC). The results are given in Table 4. When the composition of the microspheres was changed from pHEMA to HEMA/NVP in 70/30% w/w, the drug-loading capacity was more than doubled to 70 µg.

TABLE 4

The amounts of fluorescein sodium released from the different microspheres

| Type of microspheres | Total amount Fl-Na released |
|---|---|
| pHEMA | 33 µg (n = 4) |
| pHEMA/NVP | 70 µg (n = 4) |

Example 5

Flexibility of the OphthaCoil Device

The following experiment demonstrates that it is possible to fill the lumen with microspheres without adversely affecting the flexibility. This is demonstrated against 2 controls wherein coated filaments are introduced into the lumen or wherein the lumen is left empty. The experiments are performed in the dry and the hydrated state.

Figure 4:
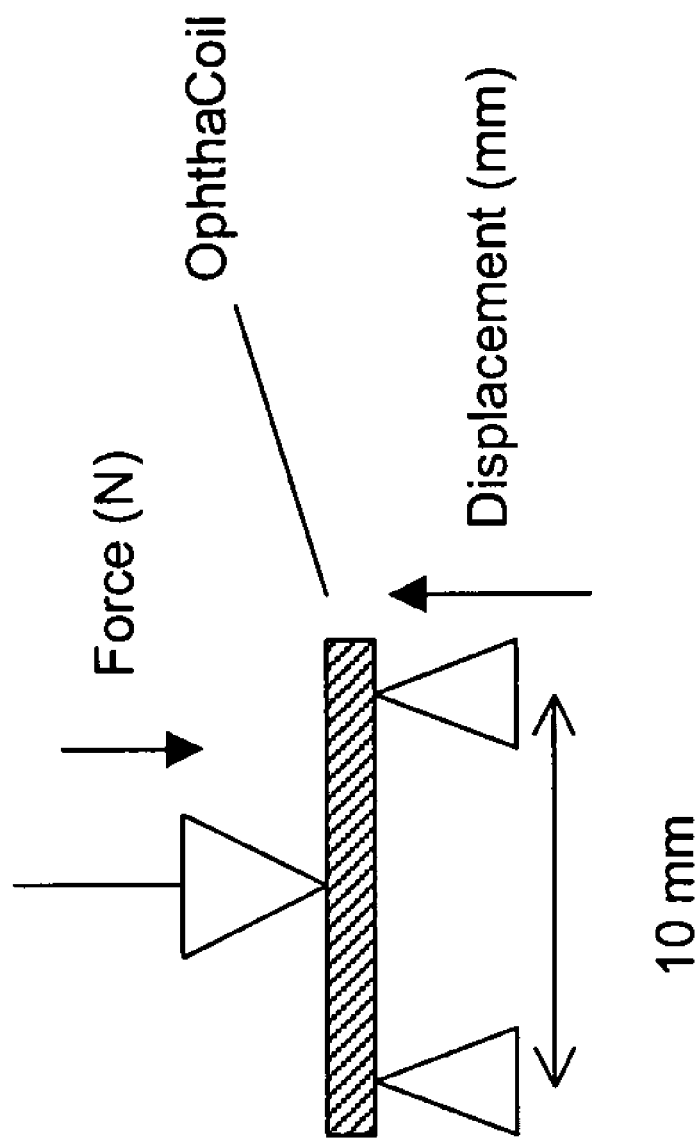

The coil's flexibility, after introducing wires or microspheres in the lumen, was measured with a three-point bending test. The coil was placed onto two clamps with a space of 10 mm. Then the coil was bent in the middle and the displacement was set on 2.5 mm. The force necessary to bend the coil was measured. The set-up is shown in FIG. 4. The coils were filled in several ways to compare the flexibility. Table 5 shows the different coils used in this experiment.

TABLE 5

The different coils used for the flexibility experiment

| Coil | Lumen |
|---|---|
| 1 | empty lumen |
| 2 | three coated metallic wires |
| 3 | pHEMA microspheres |

In the eye, the coil is placed in the conjunctival sac. Here the tear fluid will hydrate the coil. To imitate a natural environment, all three measurements were done in the dry and the hydrated state. For hydration, the coils were placed in water for one hour and the bending test was repeated with hydrated coils. All measurements (n=4) were done at room temperature.

TABLE 6

Average value of the spring-constants for the different types of coils (n = 4)

| | Dry state | | Wet state | |
|---|---|---|---|---|
| | Constant (mN/mm) | St. dev. (n = 4) | Constant (mN/mm) | St. dev. (n = 4) |
| Empty coils | 0.79 | 0.09 | 0.87 | 0.06 |
| Coils with MS | 1.60 | 0.32 | 1.69 | 0.25 |
| Coils with wires | 36.22 | 1.68 | 35.02 | 0.96 |

Figure 5:
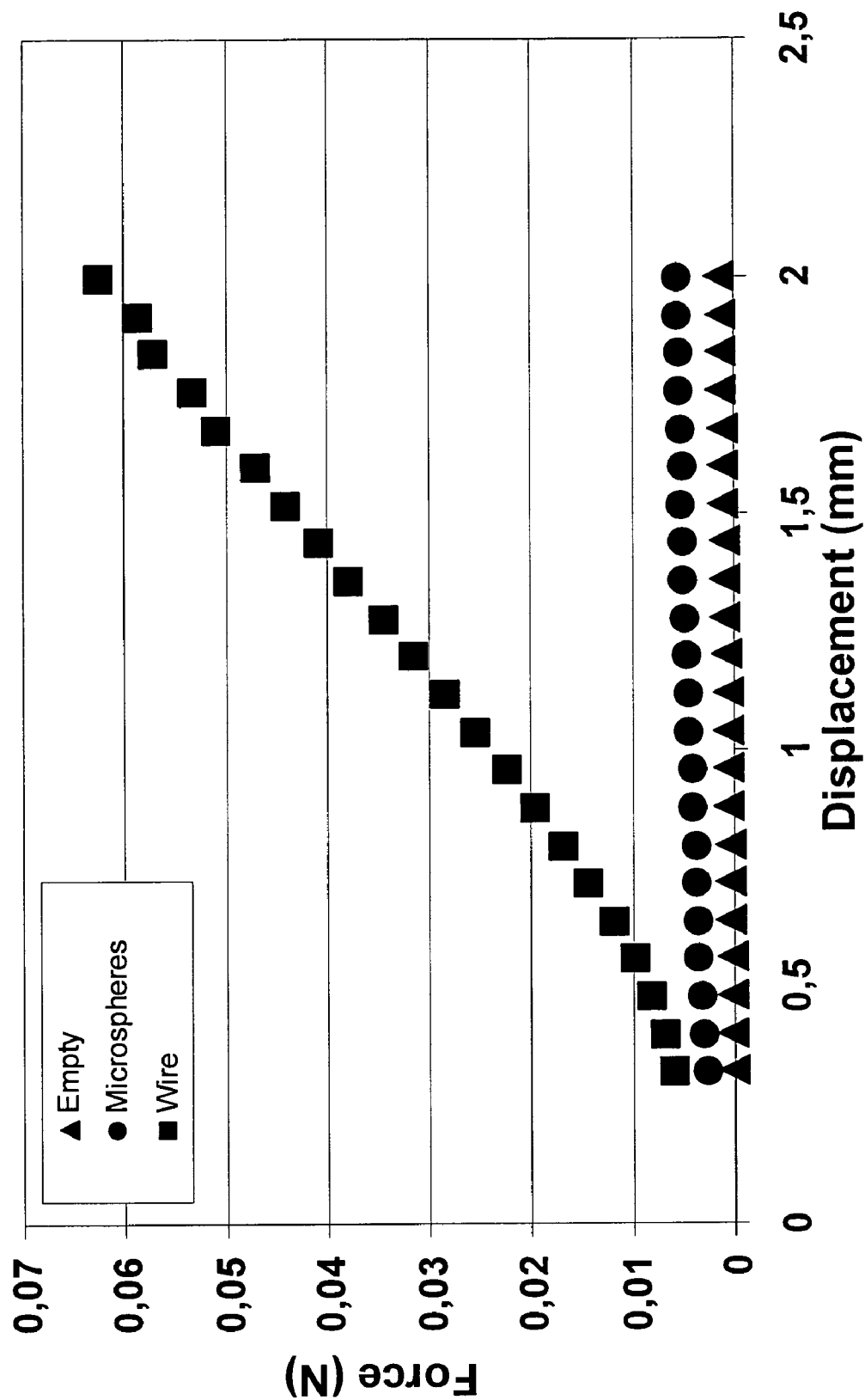

FIG. 5 shows the average values of the measurements, and Table 6 shows the spring constants of the different coils as well as their standard deviations. In the figure, the force is plotted against the displacement. The figure shows that the coil with coated wires inside the lumen has a much higher bending stiffness than the other two coils. The coil with microspheres in the lumen has a doubled bending stiffness than the empty coil. There are no significant differences between dry and wet coils.

This experiment has demonstrated that the lumen of the OphthaCoil can be filled with microspheres, without compromising the coil's flexibility. This in contrast with filaments in the lumen of the coil, which do affect the flexibility negatively.

The invention claimed is:

1. A medical device to deliver an active component at a treatment site of a patient comprising:
    a coil which includes a wire having a distal end and a proximal end, the wire being wound between the distal and proximal ends thereof such that windings of the wire form the coil;
    a coil lumen defined by the windings of the wound wire between the distal and proximal ends thereof;
    polymeric micro-particles filling the coil lumen between the distal and proximal ends thereof; and
    an active component contained within the polymeric microparticles; and
    end caps closing the micro-particle filled coil lumen at the distal and proximal ends of the wound wire, wherein
    the micro-particles have a diameter which is sufficiently small so as to be filled within the coil lumen yet sufficiently large so as to prevent the micro-particles from leaking from the coil lumen through the windings of the wire, and wherein the active component is capable of being controllably released from the polymeric micro-particles and through the windings of the wire for delivery at the treatment site.

2. A medical device according to claim 1 comprising a hydrophilic coating on the wire.

3. A medical device according to claim 1 wherein the micro-particles consist of a hydrophilic polymer.

4. A medical device according to claim 1 wherein the micro-particles are micro-spheres.

5. A medical device according to claim 1, wherein the wire is a metallic wire.

6. A medical device according to claim 1, wherein the active component is a drug.

7. A medical device according to claim 3, wherein the hydrophilic polymer is poly(2-hydroxyethyl)methacrylate (pHEMA) and/or n-vinyl pyrollidone (NVP).

8. A medical device for controlled release of a drug at a treatment site of a patient comprising a drug-containing coiled wire, wherein the coiled wire comprises:
 a wire having a distal end and a proximal end, the wire being wound between the distal and proximal ends thereof such that windings of the wire form a coil defining a coil lumen inside the wire windings,
 polymeric micro-particles filling the coil lumen between the distal and proximal ends thereof;
 a drug contained within the polymeric microparticles;
 a hydrophilic coating on the wire; and
 end caps closing the micro-particle filled coil lumen at the distal and proximal ends of the wound wire, wherein the micro-particles have a diameter which is sufficiently small so as to be filled within the coil lumen yet sufficiently large so as to prevent the micro-particles from leaking from the coil lumen through the windings of the wire, and wherein
 the drug is capable of being controllably released from the polymeric micro-particles and through the windings of the wire for delivery at the treatment site.

9. A medical device according to claim 8, wherein the micro-particles consist of a hydrophilic polymer.

10. A medical device according to claim 9, wherein the hydrophilic polymer is poly(2-hydroxyethyl)methacrylate (pHEMA) and/or n-vinyl pyrollidone (NVP).

11. A medical device according to claim 8, wherein the micro-particles are micro-spheres.

12. A medical device according to claim 8, wherein the wire is a metallic wire.

13. A medical device according to claim 1, wherein the active component is a drug.

14. A medical device according to claim 13, wherein the wire is a metallic wire.

15. A medical device according to claim 14, wherein the metallic wire includes a hydrophilic coating.

16. A medical device as in claim 2 or 15, wherein the hydrophilic coating additionally comprises the active component to provide for a more quick release of the active component as compared to release of the active component contained within the micro-particles.

\* \* \* \* \*